United States Patent [19]

Tammen

[11] Patent Number: 5,058,318

[45] Date of Patent: Oct. 22, 1991

[54] PROCESS FOR THE PRODUCTION OF LILIUM SPECIES

[76] Inventor: James F. Tammen, 109 Norle St., State College, Pa. 16802

[21] Appl. No.: 554,220

[22] Filed: Jul. 17, 1990

[51] Int. Cl.$^5$ ............................................... A01C 1/00
[52] U.S. Cl. .................................... 47/58; 47/DIG. 3
[58] Field of Search ............................................ 47/58

[56] References Cited

U.S. PATENT DOCUMENTS

| 4,338,745 | 7/1982 | Misawa et al. | 47/58 |
| 4,570,379 | 2/1986 | Oglevee et al. | 47/58 |
| 4,897,957 | 2/1990 | Oglevee et al. | 47/58 |

OTHER PUBLICATIONS

Kyte, L., "Lily, Lilium spp. Lilaceae", *Plants from Test Fibers* 1983 Timber Press, Portland, Ore., p. 98.

Krikorian, A. D., et al., "Chapter 9 Regeneration in Liliaceae, Iridaclal and Maryllidaceal", *Cell and Somatic Cell Genetics of Plants*, vol. 3, 1986, (Vasil, Editor), Academic Press, Inc., Orlando, pp. 187–204.

Hughes, K. W., "Chapter 2 Ornamental Species" Cloning Agricultural Plants via in Vitro Techniques, (Conger, Editor), CRC Press Inc., Boca Raton, Fla., pp. 5–28.

Thompson, H. C., et al., "Chapter 2D Bulb Crops", *Vegetable Crops*, 5th Ed., 1957, McGraw-Hill Book Co., New York, pp. 347–370.

Hartmann, H. T., et al., "Bulbs" *Plant Propagation Principles and Practices*, 2nd Ed., 1968 Prentice-Hall Inc., Englewood Cliffs, N.J., pp. 506–519.

Hastings, R., "Forcing Lilies for Easter Pots", The Ball Red Book, 11th Ed., Geo. J. Ball, Inc., 1968, pp. 276–283.

Laurie, A., et al., "Lily (Lilium Longilforum-Liliaceae)", *Commercial Flower Foreing*, 7th Ed., 1969 McGraw-Hill Book Co., N.Y., pp. 414–420.

*Primary Examiner*—James R. Feyrer
*Attorney, Agent, or Firm*—Saliwanchik & Saliwanchik

[57] ABSTRACT

The subject invention concerns a process for the expeditious production of members of the Lilium genus. Using the procedures described here, it is possible to produce Lilium bulbs of forcing size in less than a one-year period. Specifically, young plants are grown in a vegetative, not reproductive, state in order to produce a large bulb in only about 10 months. The young plants are obtained from pathogen-free mother plants using tissue culture techniques. Virus-free production zones can be used to ensure pathogen-free plants.

3 Claims, No Drawings

PROCESS FOR THE PRODUCTION OF LILIUM SPECIES

BACKGROUND OF THE INVENTION

Species of Lilium have become increasingly popular as flowering pot plants and cut flowers. Easter lilies (*Lilium longiflorum*) have been historically used at Easter and other religious occasions. Cultivars of other Lilium species and hybrids have become even more important in the market place. The so-called Asiatic hybrids and Oriental hybrids, among others, are the most important of these.

Lilies are grown from bulbs which, in nature, typically go through a two to three year growth cycle before they can be induced to flower. The forcing procedure usually involves a low temperature vernalization treatment which induces flower initiation. Easter lilies, in general, are forced to flower once each year for the Easter holiday. Asiatic, Oriental, and other lilies are forced to flower year-round. In order to achieve year-round flowering, bulbs are vernalized and then frozen until needed. The longer the period of time that the bulbs are frozen, the lower is the number of flowers per bulb.

Recently developed methodologies have enabled growers to shorten the growth period and to eliminate the vernalization treatment necessary before forcing for flowering, particularly for certain cultivars of *Lilium longiflorum*. Oglevee et al. describe the growth of Easter lilies in one year or less (U.S. Pat. No. 4,570,379, issued 2/18/86 to James R. Oglevee, James F. Tammen, and Wendy O. O'Donovan). The Oglevee patent describes a procedure whereby a leaf from a substantially pathogen-free lily plant is propagated in a growing medium to form a bulblet which is thereafter grown in plant form rather than bulb form. The plant is initially grown under short days to prevent flowering; then flowers are initiated through growth under long day conditions.

Unlike the subject invention, the Oglevee patent pertains primarily to the production of plants rather than bulbs. Furthermore, unlike the subject invention, Oglevee does not utilize tissue culture techniques. Tissue culture techniques facilitate the production of a large number of plants which do not exhibit phenotypic variation. Also, Oglevee does not recognize or utilize the temperature sensitivity of the Lilium bulbs or plants, nor does it involve the use of temperature and light equations to regulate growth in order to enhance the quality of the flowers and to flower lilies year-round.

BRIEF SUMMARY OF THE INVENTION

The subject invention pertains to the production of forcing-size Lilium bulbs in less than a one-year period. Specifically, tissue culture techniques are used to provide large numbers of pathogen-free, clonally identical young plants which are grown in the vegetative, not reproductive, state. Through the advantageous manipulation of temperature and photoperiod, continuous vegetative growth is achieved in order to produce the largest possible bulb in a short period of time. Because the temperature and light inputs required to maintain the plants and the bulbs in the vegetative state are quantified, the bulbs thus produced can be induced to flower either through the use of temperature and light, or both, as desired.

DETAILED DESCRIPTION OF THE INVENTION

According to the procedures of the subject invention, forcing-size Lilium bulbs can be produced in less than one year. The size and characteristics of forcing-size bulbs are well known to those skilled in the art, but, by way of example, the circumference of these bulbs is about 12.5 to 15 cm for Asiatic lilies, about 20.0 to 22.5 cm for oriental lilies, and about 17.5 to 20.0 for Easter lilies.

Initially, mother plants are grown under conditions which preclude the introduction of plant pathogens and the agents that transmit them.

These mother plants are selected for superior horticultural quality and performance, and each is grown as an identifiable clonal unit. The mother plants provide pathogen-free propagules which are of primary importance in the novel process.

Using standard procedures, propagules which index free of known pathogenic fungi, nematodes, bacteria and viruses are generated and used to produce so-called pathogen-free mother plants and bulbs. Bulb scales from these are harvested and large numbers of clonally uniform bulblets are generated using tissue culture techniques and processes as follows:

(1) Heat treating the mother bulb scales at 46° C. for 30–45 minutes.

(2) Rapidly cooling and surface sterilizing the heat treated scales by immersing them in an approximately 0.525% solution of sodium hypochlorite for 5 to 15 minutes.

(3) Using aseptic procedures, dissecting approximately 0.5 $cm^{-2}$ scale pieces from selected areas of the scales and placing them on tissue culture media with appropriate amounts of growth regulators.

(4) Growing bulbils of approximately 0.5–1.0 cm (diameter) at temperatures of 21° C. and using a 16 hour daylength (about 10 to 12 weeks).

(5) Cooling the bulbils so generated at about 5° C. for about 2–4 weeks, depending on type and cultivar.

These techniques and procedures essentially eliminate phenotypic variation within clonal lines. Central to this invention, however, the bulbils produced are set to grow continuously in the vegetative, not reproductive state. The vegetative state for tissue cultured bulbils is defined as growth of the apical meristem to produce scale, not stem, leaves. Growth in this vegetative state is induced through appropriate manipulation of temperature, light, and growth regulators. Continued vegetative growth after tissue culture and the subsequent induction of reproductive growth is dependent upon temperature and light (day length). The relationship between temperature and light may be quantified. Moreover, temperature and light under certain conditions are substitutable or interchangeable. Thus, one can either add or subtract temperature and/or light in order to get either vegetative or reproductive growth. The manipulation of the temperature/light effect to either maintain vegetative growth or to induce flowering in lilies at will and under outdoor conditions is central to this invention.

Following are examples which illustrate procedures, including the best mode, for practicing the invention. These examples should not be construed as limiting.

EXAMPLE 1

Pathogen-free Lilium bulbs of all types (Easter, Asiatic, Oriental, etc.) of the highest quality forcing size and ready to force for flowering can be produced out-of-doors in virus-free zones within ten months or less. These bulbs may be used for commercial cut flower or pot production, or for landscaping. Virus-free production zones are geographic areas wherein particular plant viruses and/or their vectors do not exist. Thus, if a population of plants free of those viruses is grown in the area, it can be grown to maturity free of those viruses. Thus, the need for expensive enclosure structures designed to prevent the introduction of these viruses is eliminated. Large areas of Florida are virus-free production zones for Lilium species, particularly those on the west coast from the Bradenton to the Naples area.

First, a mother block of lily plants of the desired types which index free of known plant pathogens, using standard indexing techniques, are grown and increased in number under conditions which preclude the introduction of plant pathogens and the agents which transmit them.

Second, using bulb scales removed from bulbs of mother plants and the tissue culture techniques described above, large numbers of clonally identical bulbils measuring about 0.5–1.0 cm in diameter can be produced within 10–12 weeks. These bulbils are generated using procedures which will cause them to grow in the vegetative state and to produce scale, not stem, leaves.

Third, the bulbils produced in tissue culture are cooled at 5° C. for a period of 2–4 weeks, depending upon type and cultivar. The skilled practitioner will determine with no difficulty the exact cooling period which is optimal for the cultivar he is growing.

Fourth, the bulbils with scale leaves and roots are transplanted from tissue culture into an artificial growing medium in small containers in the greenhouse and grown vegetatively for about 10–12 weeks. The container may be maintained by keeping the temperature at or above about 21° C., for example, and/or the dark period at about 16 hours, for example. Irradiance levels can be about 500 $\mu$mol m$^{-2}$s$^{-1}$. These growing conditions are maintained until about 6 to 8 scale leaves are produced.

Fifth, the young plants with scale leaves are transplanted into outdoor beds, under shade cloth, which have been chemically or heat treated in order to eradicate microorganisms pathogenic to lilies. These plants are grown in the vegetative state for about 16 to 24 weeks, depending upon the lily type, until a bulb of highest quality forcing size is attained. A person skilled in this art is able to readily determine the specific length of time needed in a vegetative state for a particular type of lily. The growing season may be, for example, between October and May.

At about the time that approximately 10–14 scale leaves have been produced, the apical meristem will begin to produce stem, not scale, leaves. These leaves are sensitive to temperature and to daylength.

Plants of the genus Lilium growing to produce stem leaves sense and accumulate temperature and light (daylength) inputs which regulate vegetative and reproductive growth phases. For example, temperatures over 21° C. are sensed and accumulated as units for vegetative growth; temperatures below 21° C. are sensed and accumulated as units for reproductive growth. The sum of the number of degree-hours below 21° C., but above 2° C., minus the number of degree-hours above 21° C. must be about 20,000 in order for flower initiation to occur in Asiatic lilies. Short days (dark periods of 13 hours or more) are sensed and accumulated as units for vegetative growth; long days (dark periods of about 11 hours or less) are sensed and accumulated as units for reproductive growth. Units of temperature and light can be substituted. In this example, about 20,000 temperature units may be required to induce flower initiation in Asiatic lilies; one light unit (long day) may be equal to and substitutable for about 1000 cool temperature units.

Thus, Asiatic lilies planted in October in virus-free zones in central Florida with apical meristems producing stem leaves will continue to grow vegetatively until they have accumulated about 20,000 cool temperature units. On some days, temperatures may exceed 21° C.; this will subtract from the accumulated cool temperature units. On some days the temperature may be less than 21° C. and this will add to the accumulated cool temperature units. Temperatures may be determined for each of 24 hours each day throughout the growing period, and, thus, the vegetative/reproductive state of the plants can be quantified and known continuously. Again, maintaining vegetative growth is essential for the production of bulbs of the highest possible forcing quality in the shortest possible time. Should the plants approach the threshold of cool temperature units for flower initiation during the growing period, short days will be required in order to continue vegetative growth. The number of such days needed is quantifiable.

Sixth, plants of the genus Lilium accumulate carbohydrate reserves while growing vegetatively. The amount of carbohydrate accumulated determines the number and quantity of the flowers produced. The amount of carbohydrate accumulated is directly related to light intensity and duration, given near optimum temperatures, and is generally correlated to bulb (and plant) size. By sampling bulb size, vegetative growth and the accumulation of carbohydrates can be continued until the quality of bulbs required for highest possible forcing quality is reached.

Seventh, when the bulbs have reached forcing size, they can be dug, cleaned, boxed, and stored. Because the accumulated cool temperature/light status of the bulbs is known, and because the accumulated cool temperature level will always be deficient, at the appropriate time before shipping, the deficiency can be supplied to cause flowers to be initiated. The bulbs can then be shipped for commercial forcing. Alternately, the bulbs can be shipped without supplying the deficiency. In this case, the forcer can supply the cool temperature units required through the application of temperatures below 21° C., or the use of long days, or both.

EXAMPLE 2

As an alternative to the procedure described in Example 1, the young plants which are transplanted into the field and grown at a light and temperature deficiency may be utilized for cut flower production rather than bulb production. This can be accomplished by, for example, growing the plants under a temperature and/or light regime, similar to that described in Example 1, that maintains the plants in a vegetative state until they are of forcing size and quality.

Once the plants are of forcing size, the temperature and/or light deficiency can be supplied either by temperature exposure or light exposure. This will result in flowering upon demand to meet market needs.

Alternatively, instead of originally transplanting the small plants into a field, the plants may be put in pots. The same environmental manipulations can then be carried out for the same purposes.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for producing Lilium bulbs of a size suitable for flower production in less than a one-year period, said method comprising:
   (a) producing bulbils of about 0.5 to 1.0 cm diameter by dissecting scale pieces from a mother bulb and growing said scale pieces on tissue culture media at about 21° C. with an about 16 hour daylength for about 10 to 12 weeks;
   (b) keeping the bulbils produced in step (a) at about 5° C. for about 2 to 4 weeks;
   (c) growing said bulbils vegetatively for about 10 to 12 weeks with the temperature at or above about 21° C. and/or the dark period at or above 13 hours, said vegetative growth producing a young plant and continuing until about 6 to 8 scale leaves are produced; and
   (d) growing said young plant in a vegetative state for about 16 to 24 weeks until a bulb of a size suitable for flower production is obtained.

2. The method, according to claim 1, wherein said growth of young plants in a vegetative state is maintained through the manipulation of photoperiod and temperature such that said young plants do not sense and accumulate sufficient light and temperature units to induce flowering.

3. The method, according to claim 2, wherein one cool temperature unit is defined as an hour wherein the temperature is between about 2° C. and about 21° C.; and one light unit is defined as a day with less than 13 hours of darkness; and wherein one light unit is substitutable for about 1,000 cool temperature units; and wherein vegetative growth is maintained while growing said young plants from said bulbil stage to a size suitable for flower production by keeping combined vernalization cumulative cool temperature units, and equivalent light units, at less than about 20,000.

* * * * *